US00PP35407P3

(12) United States Plant Patent
Olesen

(10) Patent No.: US PP35,407 P3
(45) Date of Patent: Oct. 3, 2023

(54) HYBRID TEA ROSE PLANT NAMED 'POULREN042'

(50) Latin Name: *Rosa hybrida*
Varietal Denomination: Poulren042

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/803,618

(22) Filed: Sep. 22, 2022

(65) Prior Publication Data

US 2023/0270027 P1 Aug. 24, 2023

(30) Foreign Application Priority Data

Sep. 24, 2021 (QZ) ..... PBR 2021/2351

(51) Int. Cl.
*A01H 5/02* (2018.01)
*A01H 6/74* (2018.01)

(52) U.S. Cl.
USPC ..... Plt./134

(58) Field of Classification Search
USPC ..... Plt./134, 104, 145
CPC ... A01H 5/02; A01H 5/00; A01H 6/74; A01H 6/749
See application file for complete search history.

(56) References Cited

PUBLICATIONS

CPVO Register 4.2.50, retrieved on Nov. 14, 2022 at https://online.plantvarieties.eu/publicConsultationDetails?registerId=20212351&denomination=poulren042, 2 pp. (Year: 2022).*
Floraland Poulsen Roser 2020, retrieved on Nov. 14, 2022 at http://flora-land.ro/floraland/wp-content/uploads/2020/10/Floraland-Trandafir-si-clematis.pdf, 18 pp. (Year: 2020).*
Poulsen Roser A/S Gisila, retrieved on Nov. 15, 2022 at https://www.poulsenroser.dk/en/roses/ShowProduct/67467?productGroup=REN, 2 pp. (Year: 2022).*

* cited by examiner

*Primary Examiner* — June Hwu

(57) ABSTRACT

A new garden rose plant of the Hybrid Tea class which has abundant, yellow flowers and attractive foliage. This new and distinct variety has shown to be uniform and stable in the resulting generations from asexual propagation.

2 Drawing Sheets

Botanical designation: *Rosa hybrida.*
Variety denomination: 'Poulren042'.

This application claims priority to Plant Breeder's Rights Application Number 2021/2351, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulren042', originated as a single seedling from the stated cross.

The new variety may be distinguished from its male pollen parent and female seed parent primarily by the following characteristics. The male pollen parent plant has white flowers while the new variety has yellow flowers. While the claimed plant has flowers with strong perfume, the female seed parent has flowers with little or no scent.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance; and
4. Strong flower fragrance.

This combination of qualities is not present in previously available commercial cultivars of this type, known to the inventor, and distinguish 'Poulren042' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulren042' was selected in the spring of 2014 by the inventor as a single plant from the progeny of the aforementioned hybridization.

Asexual reproduction of 'Poulren042' by rooted cuttings was first done by Mogens N. Olesen in the nursery in Fredensborg, Denmark in July, 2014. This initial and other subsequent asexual propagations conducted in controlled environments have demonstrated that the characteristics of 'Poulren042' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren042'.

Specifically illustrated in FIG. 1 of the drawings are open flowers viewed from above and the side, flower petals and sepals detached, showing reproductive flower parts and the receptacle, and flower buds.

Figure 1:
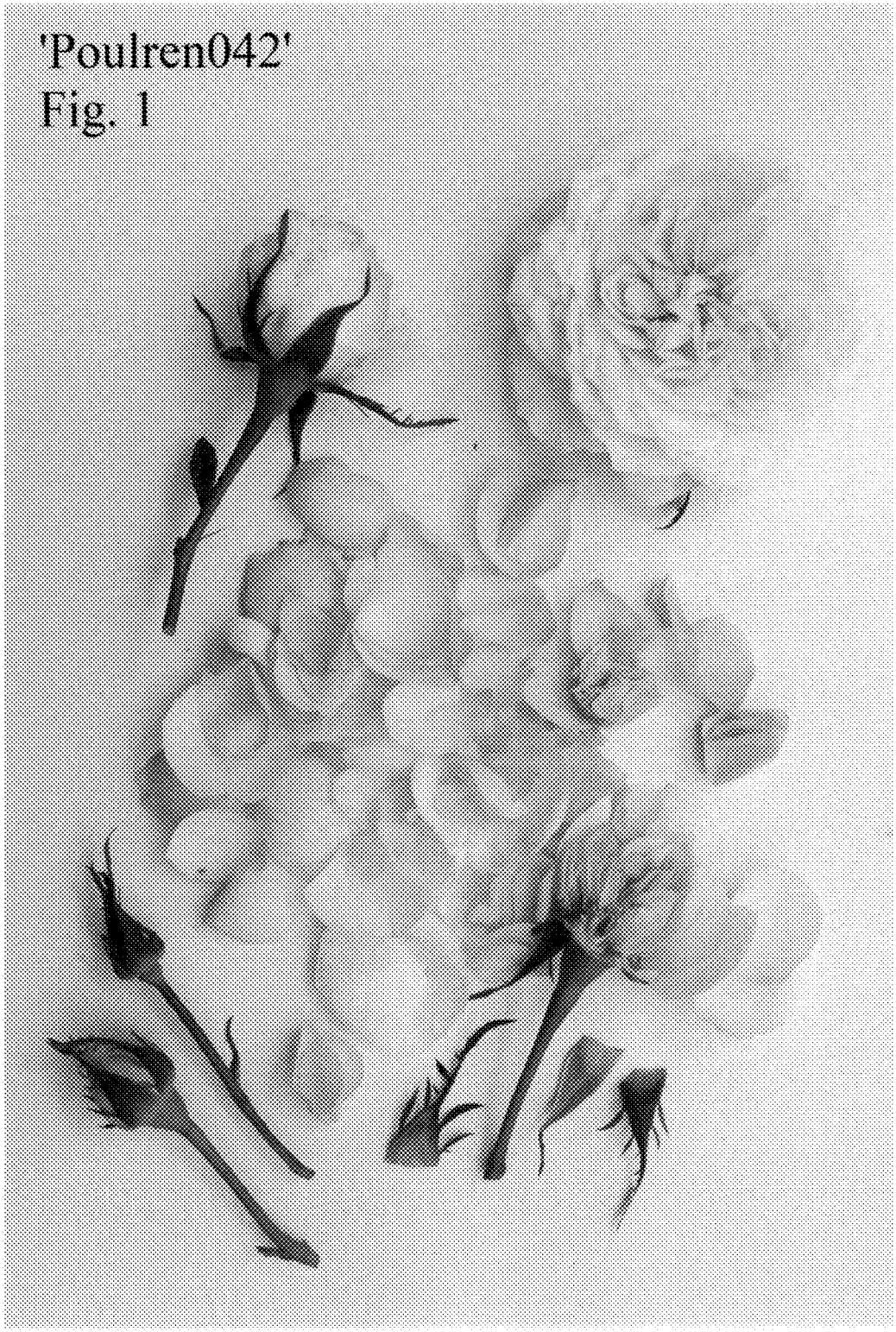
Figure 2:
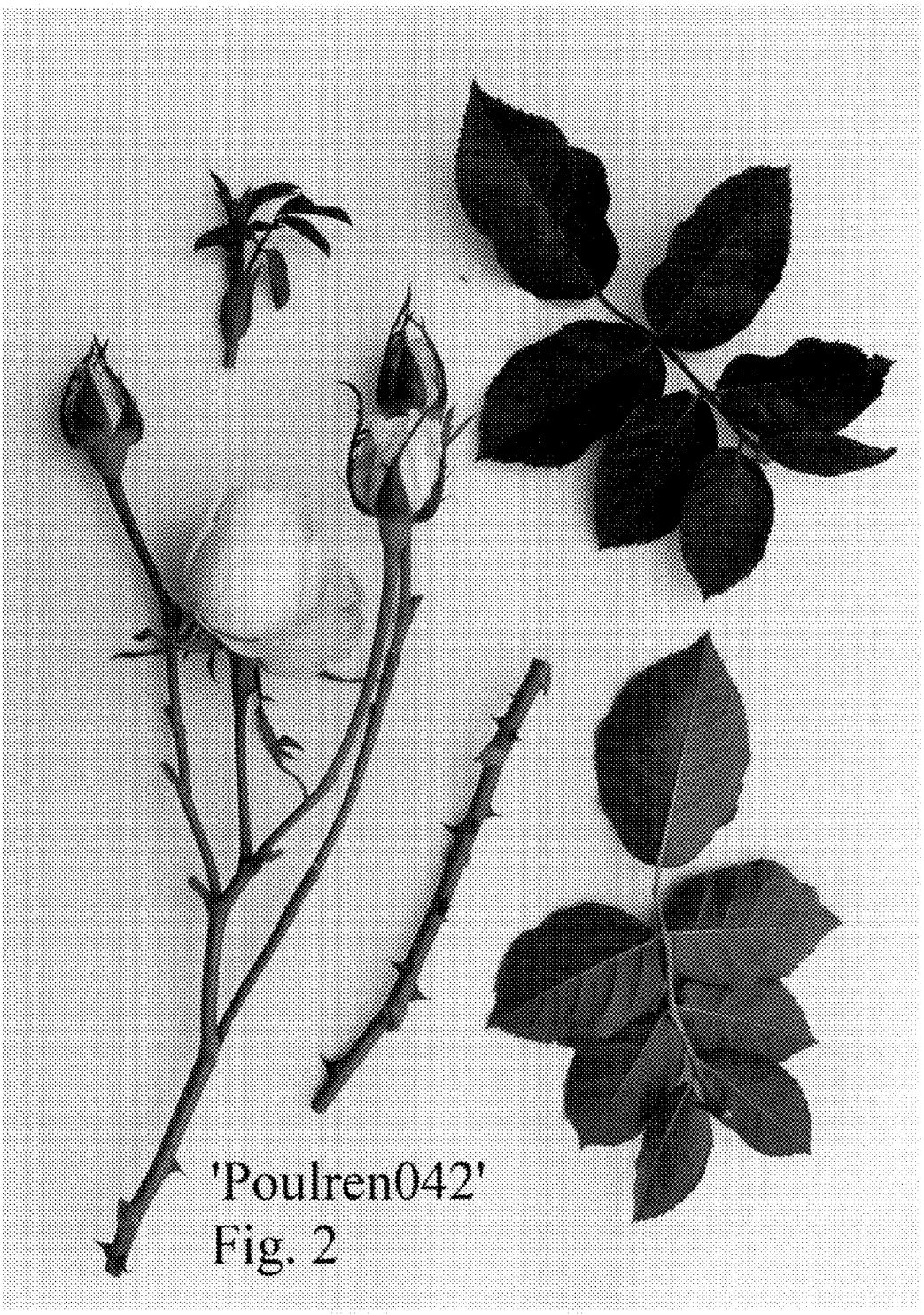

Specifically illustrated in FIG. 2 of the drawings is a cluster of flower buds and partially opened flowers on the branch, juvenile growth exhibiting anthocyanin, bare stem with prickles, and mature leaves. Plants shown are 2 years of age.

DETAILED DESCRIPTION OF THE VARIETY

The following is a description of 'Poulren042',as observed in its growth in an outdoor nursery in Odense Denmark. Observed plants are 15 months of age, and were grown on their own roots in 30 cm pots. Color references are made using The Royal Horticultural Society (London, England) Colour Chart, 2001, except where common terms of color are used.

For a comparison, several physical characteristics of the rose variety 'WEKdidusinra', U.S. Plant Pat. No. 22,540 are compared to 'Poulren042'. While the claimed plant grows to a height of 50 to 75 cm in height, the comparison variety is taller, growing 120 to 150 cm in height. The claimed plant has a petal count of 160 petals, compared to 33 to 70 petals for 'WEKdidusinra'. The comparison flower colour is described as Yellow 4C and 5D gradually diffusing toward the edge of the petals with between 155A and 155B. The claimed plant has flowers which are Yellow 9A to 10B at the center becoming White Group 155B at the margins.

FLOWER AND FLOWER BUD

Blooming habit: Continuous.

Flower bud:

- *Size*.—Upon opening, 25 mm in length from base of receptacle to end of bud. Bud diameter is 15 mm.
- *Bud form*.—Ovoid.
- *Bud color*.—As sepals divide petals are Yellow Group 2C.
- *Sepal inner surface*.—Color: Yellow-Green Group 147A and Yellow-Green Group 145B. Surface: Lightly pubescent.
- *Sepal outer surface*.—Color: Yellow-Green Group 146A with light intonations of Greyed-Red Group 178A. Texture: Smooth.
- *Sepal shape*.—Apex: Cirrhose. Base: Flat at union with receptacle.
- *Sepal margin*.—Margins have strong foliaceous appendages on three of the five sepals.
- *Sepal size*.—54 mm long, 21 mm wide.
- *Receptacle*.—Texture: Smooth. Size: 12 mm in height, 12 mm wide. Color: Yellow-Green Group 144A. Shape: Campanulate.
- *Pedicel*.—Surface: Smooth. Length: 41 mm. Diameter: 3 mm on average. Color: Yellow-Green Group 144A. Strength: Strong.
- *Peduncle*.—Length: 30 to 40 mm. Diameter: About mm. Color: Yellow-Green Group 144A. Texture: Smooth.

Flower bud development: Flower buds are borne in clusters of 3 to 5 flower buds per stem.

Flower bloom:

- *Fragrance*.—Very strong, citrus like perfume.
- *Duration*.—The blooms have a duration on the plant of approximately 14 days. Petals fall cleanly away from plant after flowers have fully matured.
- *Size*.—Flower diameter is about 100 mm when open. Flower depth is 32 mm.
- *Flower shape*.—Rosette, very double flower with many slightly overlapping petals of different sizes. Viewed from the top, flowers are round.
- *Shape of flower, side view*.—The upper portion is flat convex. The lower portion is flat.

Petalage: Under normal conditions, flowers have about 160 petals.

General tonality of flower: Open flowers are Yellow Group 4B and White Group 155B.

Petal color:

- *Upon opening, outer petals*.—Upper surface: Basal zone medium sized spot of Yellow Group 8A. Middle zone Yellow Group 8B. Marginal zone White Group 155B. Lower surface: Basal zone medium sized spot of Yellow-Orange Group 14D. Middle & marginal zone Yellow Group 4C blended with White Group 155B.
- *Upon opening, inner petals*.—Upper surface: Medium sized spot of Yellow Group 9A at basal zone. Middle and marginal zone Yellow Group 10B. Lower surface: Medium sized spot of Yellow Group 9A at basal zone. Middle and marginal zone Yellow Group 10B.
- *After opening, outer petals*.—Upper surface: At the basal zone a medium sized spot of Yellow Group 8B. The middle zone is Yellow Group 8D. Marginal zone White Group 155B. Lower surface: At the basal zone a medium sized spot of Yellow-Orange Group 14D. The middle & marginal zones are Yellow Group 4D blended with White Group 155B.
- *After opening, inner petals*.—Upper surface: At the basal zone a medium sized spot of Yellow Group 9B. The middle and marginal zones are Yellow Group 10D. Lower surface: At the basal zone a medium sized petal spot of Yellow Group 9B. The middle and marginal zones are Yellow Group 10D.

Petals:

- *Petal reflex*.—Slightly reflexed.
- *Margin*.—Entire and uniform. Moderate undulations.
- *Shape*.—Broad and elliptic. Apex shape: Rounded with single point. Base shape: Acute and rounded.
- *Size*.—About 46 (l) mm×51 mm (w).
- *Texture*.—Smooth.
- *Thickness*.—Average.

Petaloids:

- *Size*.—18 mm (l) by 8 mm (w).
- *Quantity*.—About 20.
- *Shape*.—Elliptical with an acute base and apex. Many petaloids fused with anthers and filaments.
- *Color*.—Yellow Group 13B on the upper and lower surface.

Reproductive flower parts:

- *Pollen*.—None observed.
- *Anthers*.—Size: 2 mm in length. Color: White Group 155A. Quantity: About 8. Many of the anthers are fused with petaloids.

*Filaments*.—Color: Yellow-Green Group 4D Length: 5 mm.

*Pistils*.—Length: 14 mm. Quantity: 29 on average.

*Stigmas*.—Color: Yellow-White Group 158B.

*Styles*.—Color: Red-Purple Group 58C.

*Location of stigmas*.—Level in location relative to the length of the filaments and the height of the anthers.

*Hips*.—None Observed.

PLANT

Plant growth: Upright. Plants are 50 to 75 cm in height, and 45 to 60 cm wide.

Stems:

*Color of juvenile growth*.—Yellow-Green Group 144B.

*Color of mature growth*.—Yellow-Green Group 146B.

*Length*.—Canes are about 20 cm from the base of the plant to the flowering portion.

*Diameter*.—About 6 mm.

*Internodes*.—On mature canes about 35 mm between nodes.

*Surface texture*.—Young wood: Smooth. Older wood: Smooth.

Long prickles:

*Incidence*.—About 10 prickles per 10 cm of stem.

*Size*.—Average length of prickles on mature stems is 10 mm.

*Shape*.—Upper portion is linear. Lower portion is concave.

*Color*.—Juvenile prickles: Mature prickles: Greyed-Purple Group 183B.

Plant foliage:

*Compound leaf*.—165 mm (l)×130 (w).

*Quantity*.—2 leaves per 10 cm of stem on average.

*Leaf bearing angle to the stem*.—45 degrees.

*Color of juvenile foliage*.—Upper side: Yellow-Green Group 146B with intonations of Greyed-Purple Group 183C. Lower side: Yellow-Green Group 144A Greyed-Purple Group 183B.

*Color of mature foliage*.—Upper side: Yellow-Green Group 147A. Lower side: Yellow-Green Group 146B.

Plant leaves and leaflets:

*Stipules*.—Size: 20 mm long, 2 mm wide. Quantity: 2 per compound leaf. Shape: Linear, slightly broad based with outward extending apices. Margins: Finely serrated. Color:

*Petiole*.—Length: About 20 mm. Diameter: 2 mm. Upper surface color: Yellow-Green Group 144A. Lower surface color: Yellow-Green Group 144A.

*Rachis*.—Length: 65 mm on average. Upper surface color: Yellow-Green Group 144A. Lower surface color: Yellow-Green Group 144A.

*Leaflet*.—Quantity: Normally 7 leaflets. Margins: Serrated. Size: Terminal leaflets are about 80 mm long, 56 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew Peronospora sparsa, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren042' substantially as described and illustrated herein.

* * * * *

'Poulren042'

'Poulren042'